(12) United States Patent
Karimabadi (10) Patent No.: US 10,943,142 B2
(45) Date of Patent: Mar. 9, 2021

(54) REMOVAL OF MASKING STRUCTURES IN IMAGES FOR THE DETECTION OF ANOMALIES

(71) Applicant: CureMetrix, Inc., La Jolla, CA (US)

(72) Inventor: Homayoun Karimabadi, Del Mar, CA (US)

(*) Notice: Subject to any disclaimer, the term of this patent is extended or adjusted under 35 U.S.C. 154(b) by 0 days.

(21) Appl. No.: 16/336,428

(22) PCT Filed: Sep. 22, 2017

(86) PCT No.: PCT/US2017/053099
§ 371 (c)(1),
(2) Date: Mar. 25, 2019

(87) PCT Pub. No.: WO2018/057990
PCT Pub. Date: Mar. 29, 2018

(65) Prior Publication Data
US 2019/0228257 A1  Jul. 25, 2019

Related U.S. Application Data

(60) Provisional application No. 62/399,214, filed on Sep. 23, 2016.

(51) Int. Cl.
| G06K 9/62 | (2006.01) |
| A61B 5/055 | (2006.01) |
| G06T 7/00 | (2017.01) |
| G01R 33/56 | (2006.01) |
| A61B 6/00 | (2006.01) |
| A61B 8/08 | (2006.01) |

(52) U.S. Cl.
CPC ............ *G06K 9/6203* (2013.01); *A61B 5/055* (2013.01); *A61B 6/502* (2013.01); *A61B 8/0825* (2013.01); *G01R 33/5608* (2013.01); *G06T 7/0016* (2013.01); *G06T 2207/10116* (2013.01); *G06T 2207/10128* (2013.01); *G06T 2207/30068* (2013.01)

(58) Field of Classification Search
CPC ...... G06K 9/6203; A61B 5/055; A61B 6/502; A61B 8/0825; G01R 33/5608; G06T 7/0012–0016
See application file for complete search history.

(56) References Cited

U.S. PATENT DOCUMENTS

| 6,409,668 B1 * | 6/2002 | Wollschlaeger | ..... | A61B 8/0825 600/443 |
| 6,594,378 B1 * | 7/2003 | Li | ......................... | G06T 3/0068 128/922 |

(Continued)

*Primary Examiner* — Sean T Motsinger
(74) *Attorney, Agent, or Firm* — Torrey Pines Law Group, PC (57) ABSTRACT

A method includes obtaining a first image of a patient procured during an X-ray, analyzing the first image for one or more unmasked anomalies, shifting the first image to provide a shifted image, obtaining a residual image comprising a combination of the first image and the shifted image, and analyzing the residual image for one or more masked anomalies, where the one or more masked anomalies include anomalies that went undetected in the analysis of the first image for the one or more unmasked anomalies due to a presence of one or more masking features in the first image.

24 Claims, 7 Drawing Sheets

(56) References Cited

U.S. PATENT DOCUMENTS

| | | | | |
|---|---|---|---|---|
| 7,043,066 B1* | 5/2006 | Doi | ............................ | G06T 5/50 |
| | | | | 382/132 |
| 2006/0002633 A1* | 1/2006 | Takeo | ........................ | G06T 7/30 |
| | | | | 382/294 |
| 2006/0274145 A1* | 12/2006 | Reiner | .................... | G06F 19/321 |
| | | | | 348/62 |
| 2010/0195886 A1* | 8/2010 | Bertens | .................... | G06T 7/269 |
| | | | | 382/131 |
| 2011/0164725 A1* | 7/2011 | Morita | .................... | A61B 6/583 |
| | | | | 378/62 |
| 2019/0355125 A1* | 11/2019 | Park | ........................ | G06T 7/0012 |

* cited by examiner

REMOVAL OF MASKING STRUCTURES IN IMAGES FOR THE DETECTION OF ANOMALIES

CROSS-REFERENCE TO RELATED APPLICATIONS

This application claims priority from U.S. Provisional Application Ser. No. 62/399,214 filed on Sep. 23, 2016, which is incorporated herein by reference in its entirety.

FIELD

The present disclosure generally relates to devices, systems, and methods for removing masking structures in images, e.g., to assist in the detection of an anomaly or other feature of interest.

BACKGROUND

One of the challenges with identifying and classifying an anomaly in an image, and particularly a medical image, is the presence of features and structures that can mask the presence of the anomaly. For example, in mammography, dense breast tissue may mask the presence of cancer or a mass in an X-ray image, which can reduce the efficacy of mammography as a cancer screening technique in women having dense breast tissue. Another example of an unwanted structure masking the presence of an anomaly may include a lung X-ray image, where a rib can appear as white in an image and can hide a lesion. There remains a need for improved removal of masking structures in images, e.g., for detecting and classifying an anomaly.

SUMMARY

What is provided is a method comprising obtaining a first image, analyzing the first image to detect one or more unmasked anomalies, shifting the first image to provide a second shifted image, comparing the first image and second shifted image, obtaining a residual image comprising a combination of the first image and the second shifted image, and analyzing the residual image for one or more masked anomalies, the one or more masked anomalies comprising anomalies that went undetected in the analysis of the first image for the one or more unmasked anomalies due to a presence of one or more masking features in the first image. In one aspect, the first image can be a medical image. In another aspect, the image is procured by X-ray radiography, Magnetic Resonance Imaging, positron emission tomography, single-photon emission computed tomography, ultrasound, thermography, or photography.

In yet another aspect, a method is provided which includes obtaining a first X-ray image, analyzing the first image for one or more unmasked anomalies, shifting the first image to provide a second shifted image, obtaining a residual image comprising a combination of the first image and the second shifted image, and analyzing the residual image for one or more masked anomalies, where the one or more masked anomalies include anomalies that went undetected in the analysis of the first image for the one or more unmasked anomalies due to a presence of one or more masking features in the first image.

These and other features, aspects and advantages of the present teachings will become better understood with reference to the following description, examples, and appended claims.

BRIEF DESCRIPTION OF THE DRAWINGS

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein

DETAILED DESCRIPTION

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," "substantially," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

In general, described herein are devices, systems, and methods for removing masking structures in images, e.g., to assist in the detection and identification of an anomaly or other feature of interest.

An anomaly may be any feature of interest in an image, e.g., a medical image. The anomaly may also or instead include an object, area, region, feature, data point, piece of information, etc., of interest. For example, the anomaly may include without limitation one or more of a calcification (or a cluster of calcifications), a lesion, a mass, a tumor, and the like, e.g., in a medical image, such as those images procured by X-ray radiography, Magnetic Resonance Imaging, positron emission tomography, single-photon emission computed tomography, ultrasound, thermography, or photography. The anomaly may also or instead include other physiological anomalies as known in the art.

The anomaly may be masked within an image, where masking may include the anomaly being covered, obscured, hidden, or the like. The anomaly may be fully masked, partially masked, or unmasked in embodiments.

The masking structures may include without limitation one or more of tissue, bone, cartilage, glands, arteries, veins, lymph nodes, ligaments, and the like.

One of the challenges in the identification and classification of an anomaly in a medical image is the presence of features/structures that may mask the presence of the anomaly. By way of example, in mammography, dense breast tissue can mask the presence of cancer in an X-ray image, thereby reducing the efficacy of mammography as a cancer screening technique in women with dense breasts. Or in case of a lung X-ray image, a rib may appear as white in an X-ray image where such a rib can hide or obscure lesions. The present disclosure includes techniques for removing unwanted masking features in an image, thereby more clearly exposing an anomaly. Moreover, in addition to an increase in sensitivity, the specificity may be enhanced as the aforementioned masking feature removal process may also lead to a significant reduction in false positive cancer indications.

An initial motivation for devices, systems, and methods described herein was to address the so-called "dense breast problem" in mammography—i.e., how to detect cancer in the presence of unwanted masking features such as those found in relatively dense breasts. In the case of mammography, the unwanted masking features may include normal breast features such as mammary glands, arteries, veins, lymph nodes, ligaments (e.g., Cooper's ligaments), among others. Particularly problematic among the unwanted masking features may be the gland tissue or so-called terminal ductal lobular unit (TDLU) that make and drain milk and supportive tissues that surrounds the gland. Women with relatively dense breasts generally have more gland tissue that can appear as white on an X-ray. Because cancer may also show as white on an X-ray, the presence of cancer can be masked in relatively dense breasts.

In order to remove a masking feature (e.g., gland tissue) while retaining an anomaly of interest (e.g., cancer), a technique includes shifting the image and then taking the residual of the shifted image and the original unshifted image. The shift can take on several forms such as rotation about a point by, for example, 0.000001 degrees, 0.00001 degrees, 0.0001 degrees, 0.001 degrees, 0.01 degrees, 0.1 degrees, 1 degree, 2 degrees, 3 degrees, 4 degrees, 5 degrees, 6 degrees, 7 degrees, 8 degrees, 9 degrees, or 10 degrees. In another example, a shift can be generated by displacing the shifted image by a certain number of pixels in a given direction. The shift can be global where the same shift is applied to every point in the image, or the shift can be a local shift where a different shift is applied to different parts of the image.

In a non-limiting example, a shift can be around a nipple. In addition, a shift can be around a centroid of a mass.

A residual image can be created by combining the shifted image and original unshifted image. This can include subtracting the shifted image from the original unshifted image. For example, if a pixel in the original unshifted image comprises a value, then the value of a pixel of the shifted image overlaying a pixel of the original unshifted image will be subtracted. Those of skill in the art will recognize that a grayscale range from white to black may be represented as a range from 0 (total absence, black) and 1 (total presence, white), with any fractional values in between. Therefore, if a pixel of the shifted image comprises a value of 0.75 and it overlays a pixel of the original unshifted image having a value of 0.25, then a residual image can be generated whereby that pixel will have a value of 0.50 (0.75 minus 0.25=0.50). Such subtraction of the combined images (in this example, a superimposed shifted image overlaying the original image) can be conducted on every pixel to generate a residual image. Those of skill in the art will recognize other ways of combining images and generating a residual image.

Example 1

An example will now be described. The example uses images obtained from Padhy A K, Kok T Y, Ng D, *The density factor: The enigma of dense breast*, WORLD J. NUCL. MED. 2012; 11:45-6, which is included as Appendix A and is hereby incorporated by reference in its entirety.

Figure 1A:
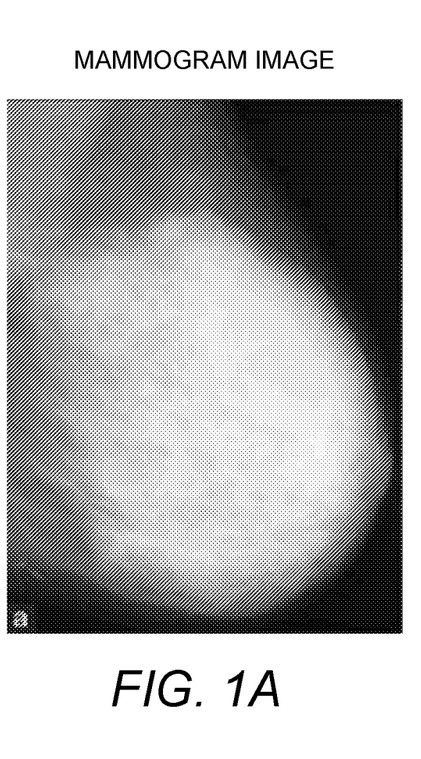
FIG. 1A shows a mammogram image of a breast.

FIG. 1A shows a mammogram image of a breast. Specifically, FIG. 1A shows a mammogram image for a relatively dense breast taken from the aforementioned article in which the authors discuss the failings of mammograms for dense breast and suggest the use of scintimammography (not as a replacement for screening mammograms but as a second step for high risk women with dense breasts). In the figure, the cancer is completely hidden by the presence of dense breast tissue.

Figure 1B:
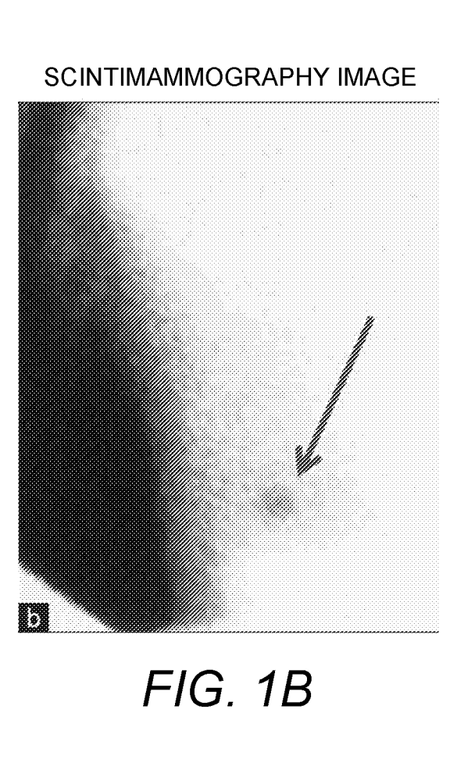
FIG. 1B shows a scintimammography image of the breast of FIG. 1A.

FIG. 1B shows a scintimammography image of the breast of FIG. 1A. Specifically, FIG. 1B shows the cancer using the scintimammography, which is a different imaging modality than mammography and generally cannot be used for routine screening.

The aforementioned article describes FIGS. 1A and 1B as follows: "Woman with palpable node in right breast inferior outer quadrant. (a) X-ray mammogram is of no value due to dense breast. (b) Scintimammography with Tc-99m Sestamibi unequivocally demonstrates a small, discrete focus of increased radiotracer uptake in the right breast, consistent with breast cancer. Histopathology: Ductal infiltrating carcinoma."

Figure 2A:
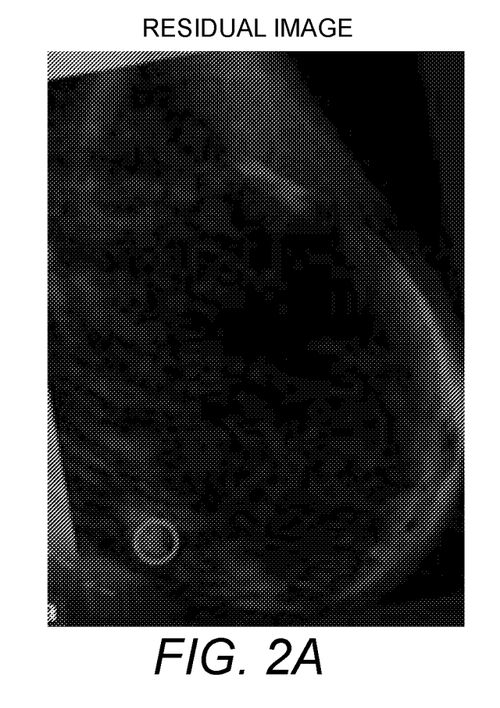
FIG. 2A shows a residual mammogram image of a breast.
Figure 2B:
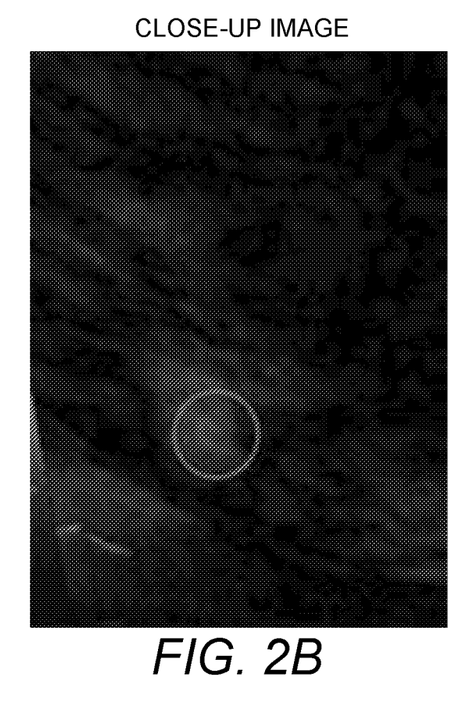
FIG. 2B shows a close-up view of the residual mammogram image.

FIG. 2A shows a residual image generated by superimposing a first image of a breast with a shifted mammogram image of a breast. As shown by FIGS. 2A and 2B, using a shift (e.g., a global shift such as a rotation, which is the case in FIG. 2A) and taking the residual image may reveal an anomaly such as cancer.

FIG. 2B shows a close-up view of the residual mammogram image. Specifically, FIG. 2B shows the zoomed-in area of the part of the image in FIG. 2A where cancer is found.

Implementations have general utility and can be used in a number of ways including without limitation as a visual tool and as hardware that uses such shifts. For example, when used as a visual tool, a radiologist could interactively apply different shifts to an image to explore the presence of cancer that may otherwise not be visible. Also, hardware could be designed to make use of the shift, e.g., by performing an imaging technique implementing the shift.

Figure 3:
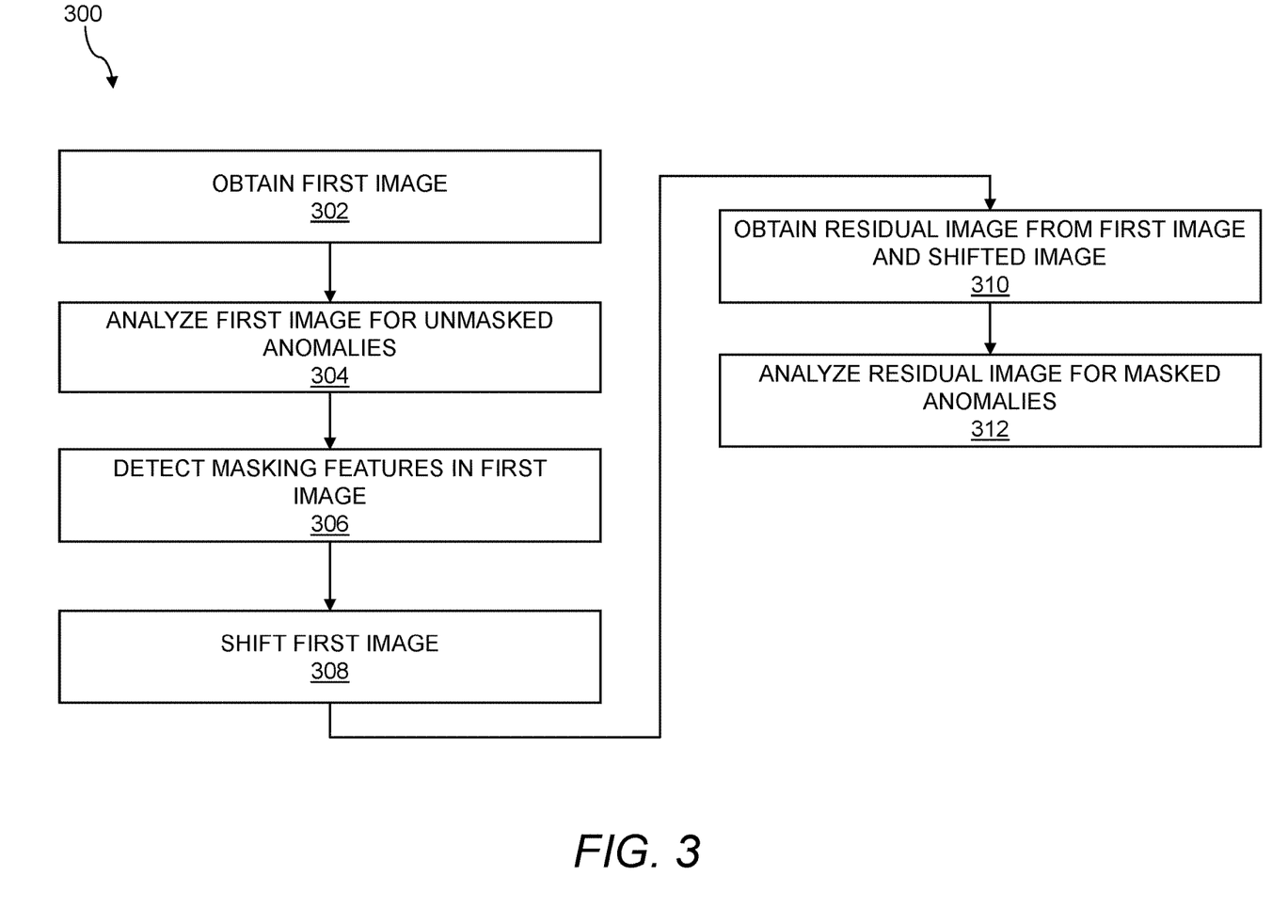
FIG. 3 is a flow chart of a method for removing masking structures in images.

FIG. 3 is a flow chart of a method for removing masking structures in images.

As shown in step 302, the method 300 may include obtaining a first image of a patient, e.g., an X-ray image. The first image may include a breast of the patient procured during a mammogram. The first image may instead be a lung X-ray image.

As shown in step 304, the method 300 may include analyzing the first image for one or more unmasked anomalies.

As shown in step 306, the method 300 may include detecting one or more masking features in the first image. A stated above, the first image may include a breast of the patient procured during a mammogram. In such an aspect, the one or more masking features may include a "normal" breast feature. The normal breast feature may include one or more of a mammary gland, an artery, a vein, a lymph node, a ligament, a terminal ductal lobular unit (TDLU), and supportive tissue for the TDLU. The one or more masking features may also or instead include relatively dense breast tissue.

A stated above, the first image may be a lung X-ray image. In such an aspect, the one or more masking features may include a rib.

As shown in step 308, the method 300 may include shifting the first image to provide a shifted image. Shifting the first image may include rotating the first image about a point. Shifting the first image may also or instead include displacement of the first image by a predetermined amount in a predetermined direction. The predetermined amount may include a certain number of pixels. Shifting the first image may include a global shift where the same shift is applied to every point in the first image. Shifting the first image may instead include a local shift, e.g., where a different shift is applied to different parts of the first image. Shifting the first image may thus include applying a plurality of different shifts to the first image.

As shown in step 310, the method 300 may include obtaining a residual image comprising a combination of the first image and the shifted image. The residual image may include the shifted image overlaid on the first image, and subtracting the difference. The residual image may instead include the first image overlaid on the shifted image, and subtracting the difference.

As shown in step 312, the method 300 may include analyzing the residual image for one or more masked anomalies. The one or more masked anomalies may include anomalies that went undetected in the analysis of the first image (i.e., the analysis for the one or more unmasked anomalies) due to a presence of one or more masking features included in the first image.

Anomalies may include one or more of a calcification, a cluster of calcifications, a lesion, a mass, and a tumor. Masking features may include one or more of tissue, a bone, cartilage, a gland, an artery, a vein, a lymph node, and a ligament.

In an aspect, a computer program product may include computer executable code embodied in a non-transitory computer readable medium that, when executing on one or more computing devices, performs the steps of obtaining a first X-ray image, analyzing the first image for one or more unmasked anomalies, shifting the first image to provide a shifted image, obtaining a residual image comprising a combination of the first image and the shifted image, and analyzing the residual image for one or more masked anomalies, where the one or more masked anomalies include anomalies that went undetected in the analysis of the first image for the one or more unmasked anomalies due to a presence of one or more masking features in the first image.

In another aspect, a system may include an imaging device and a computing device in communication with the imaging device. The computing device may include a processor and a memory, where the memory bears computer executable code configured to perform the steps of obtaining a first image of a patient procured during an X-ray, analyzing the first image for one or more unmasked anomalies, shifting the first image to provide a shifted image, obtaining a residual image comprising a combination of the first image and the shifted image, and analyzing the residual image for one or more masked anomalies, where the one or more masked anomalies include anomalies that went undetected in the analysis of the first image for the one or more unmasked anomalies due to a presence of one or more masking features in the first image. In an aspect, the computing device is integral with the imaging device.

Although certain embodiments discussed herein are described for the specific use case of breast cancer, the devices, systems, and methods discussed herein can be adapted for other cancers including without limitation brain, lung, liver, prostate, bone, cervical, colon, leukemia, Hodgkin disease, kidney, lymphoma, oral, skin, stomach, testicular, thyroid, and so forth. Furthermore, although embodiments generally described herein are directed to the use case of medical images of human tissue, the embodiments may also or instead be applicable to animal tissue, for example.

In general, the devices, systems, and methods discussed herein may utilize medical image analysis, which may be automated through the use of various hardware and software as described herein. The medical image analysis techniques discussed herein may thus be used for removing masking structures in images, e.g., to assist in the detection of an anomaly or other feature of interest.

Figure 4:
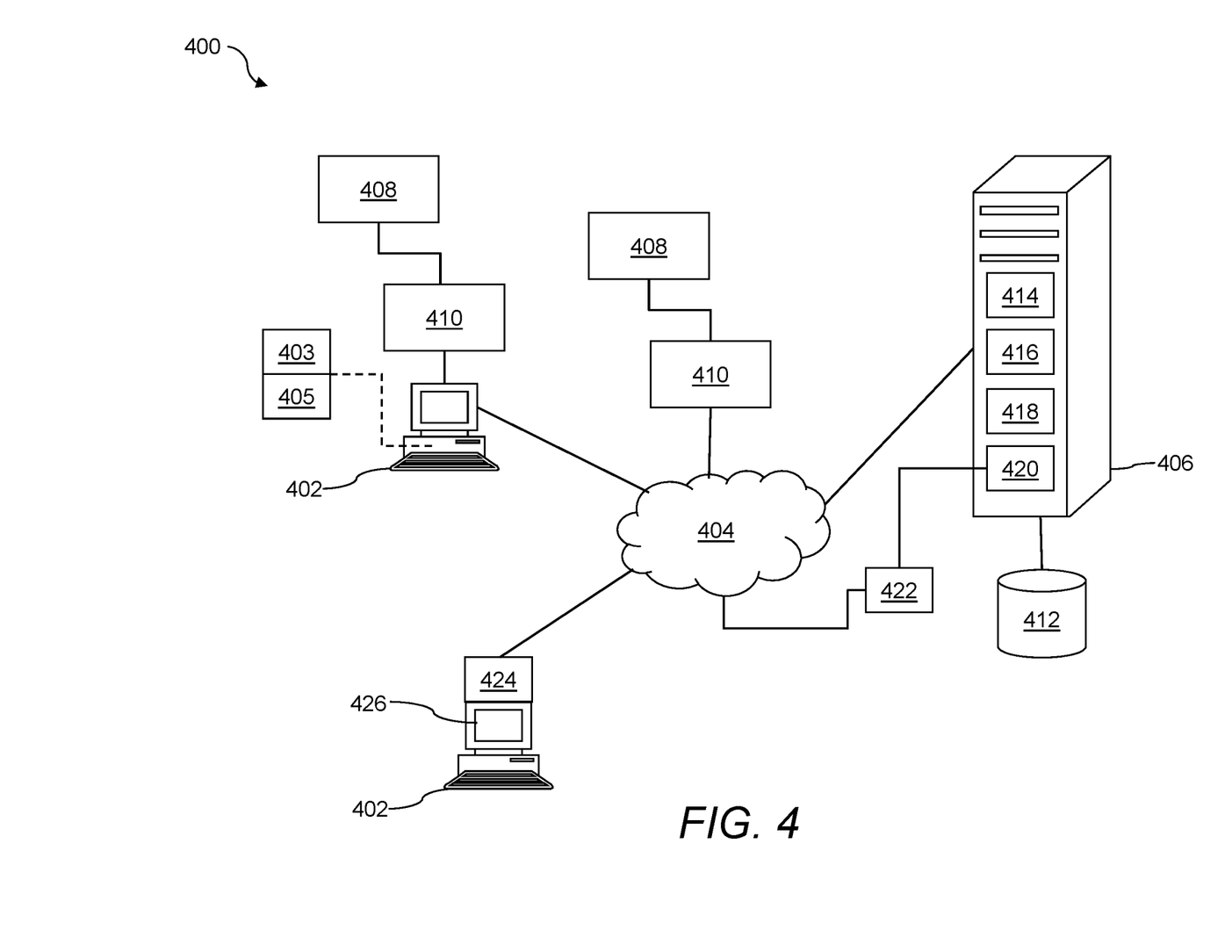
FIG. 4 illustrates a networked system for removing masking structures in images.

FIG. 4 illustrates a networked system for removing masking structures in images. As shown in the figure, the system 400 may include a client server implementation of removing masking structures in images, e.g., to assist in the detection of an anomaly or other feature of interest. The system 400 may include one or more computing devices 402 that are each used by a user or an administrator to couple to and interact with, over a network 404, a backend component 406. Although a client server/web implementation of the system 400 is shown, the system 400 may also be implemented using a software as a service (SaaS) model, a standalone computer, and other computer architectures.

The one or more computing devices 402 may include a processor based computing device that has at least one processor 403, a memory 405, persistent storage, a display, and communication circuits so that each computing device 402 can communicate with the backend component 406, display information related to images, submit pieces of medical information (e.g., images) to the backend component 406, or otherwise interact with the backend component 406 or another component of the system 400. For example, the computing device 402 may include without limitation a smartphone device, a tablet computer, a personal computer, a laptop computer, a terminal device, a cellular phone, an imaging device, and the like. In some embodiments, the computing device 402 may execute an application, such as a known browser application or mobile application, that facilitates the interaction of the computing device 402 with the backend component 406. The one or more computing devices 402 may also or instead include other devices, for example including client devices such as a computer or computer system, a Personal Digital Assistant, a mobile phone, or any other mobile or fixed computing device.

The computing device 402 may include a desktop computer workstation. The computing device 402 may also or instead be any device suitable for interacting with other devices over a network 404, such as a laptop computer, a desktop computer, a personal digital assistant, a tablet, a mobile phone, a television, a set top box, a wearable computer, and the like. The computing device 402 may also or instead include a server or it may be disposed on a server, such as any of the servers described herein.

The computing device 402 may be used for any of the entities described herein. In certain aspects, the computing device 402 may be implemented using hardware (e.g., in a desktop computer), software (e.g., in a virtual machine or the like), or a combination of software and hardware. The computing device 402 may be a standalone device, a device integrated into another entity or device, a platform distributed across multiple entities, or a virtualized device executing in a virtualization environment.

In general, the computing device 402 may include a processor 403, a memory 405, a network interface 424, a data store, and one or more input/output interfaces. The computing device 402 may further include or be in communication with peripherals and other external input/output devices that might connect to the input/output interfaces.

The processor 403 may be any processor or other processing circuitry capable of processing instructions for execution within the computing device 402 or system 400. The processor 403 may include a single-threaded processor, a multi-threaded processor, a multi-core processor and so forth. The processor 403 may be capable of processing instructions stored in the memory 405 or the data store.

The memory 405 may store information within the computing device 402. The memory 405 may include any volatile or non-volatile memory or other computer-readable medium, including without limitation a Random Access Memory (RAM), a flash memory, a Read Only Memory (ROM), a Programmable Read-only Memory (PROM), an Erasable PROM (EPROM), registers, and so forth. The memory 405 may store program instructions, program data, executables, and other software and data useful for controlling operation of the computing device 402 and configuring the computing device 402 to perform functions for a user. The memory 405 may include a number of different stages and types of memory for different aspects of operation of the computing device 402. For example, a processor may include on-board memory and/or cache for faster access to certain data or instructions, and a separate, main memory or the like may be included to expand memory capacity as desired. All such memory types may be a part of the memory 405 as contemplated herein.

The memory 405 may, in general, include a non-volatile computer readable medium containing computer code that, when executed by the computing device 402 creates an execution environment for a computer program in question, e.g., code that constitutes processor firmware, a protocol stack, a database management system, an operating system, or a combination of the foregoing, and/or code that performs some or all of the steps set forth in the various flow charts and other algorithmic descriptions set forth herein. While a single memory 405 is depicted, it will be understood that any number of memories may be usefully incorporated into the computing device 402. For example, a first memory may provide non-volatile storage such as a disk drive for permanent or long-term storage of files and code even when the computing device 402 is powered down. A second memory such as a random access memory may provide volatile (but higher speed) memory for storing instructions and data for executing processes. A third memory may be used to improve performance by providing higher speed memory physically adjacent to the processor 403 for registers, caching, and so forth. The processor 403 and the memory 405 can be supplemented by, or incorporated in, logic circuitry.

The network 404 may include a communications path such as a wired or wireless network that uses a communications protocol and a data protocol, such as HTTP or HTTPS and HTML or JSON or REST, to allow each computing device 402 to interact with the backend component 406. The network 404 may be a wired network, a wireless computer network, a wireless digital data network, a cellular wireless digital data network, or a combination of these networks that form a pathway between each computing device 402 and the backend component 406.

The network 404 may also or instead include any data network(s) or internetwork(s) suitable for communicating data and control information among participants in the system 400. This may include public networks such as the Internet, private networks, and telecommunications networks such as the Public Switched Telephone Network or cellular networks using third generation cellular technology (e.g., 3G or IMT-2000), fourth generation cellular technology (e.g., 4G, LTE. MT-Advanced, E-UTRA, etc.) or WiMax-Advanced (IEEE 802.16m)) and/or other technologies, as well as any of a variety of corporate area, metropolitan area, campus or other local area networks or enterprise networks, along with any switches, routers, hubs, gateways, and the like that might be used to carry data among participants in the system 400. The network 404 may also include a combination of data networks, and need not be limited to a strictly public or private network. The participants in the system 400 may each be configured with a network interface 424 for communications over the network.

A user 408 of the system 400 may be a patient, a doctor, a radiologist, a health care organization, an image analyst, and the like. The user 408 may, using the computing device 402, submit one or more pieces of medical information 408 (e.g., an image) for analysis by the system 400 and/or receive, e.g., from the backend component 406, information based on the received pieces of medical information 410. The backend component 406 may include storage 412 coupled to the backend component 406 (e.g., a memory, a database, and the like) that may store various data associated with the system 400 including a plurality of pieces of medical information 410 that may be used for analysis and processing as described herein, user data associated with the system, and the like. The storage 412 may be implemented using a known software based or hardware based storage system.

The backend component 406 may be implemented using one or more computing resources including without limitation a processor 414, a memory 416, persistent memory/storage, and the like. By way of example, each computing resource may be a blade server, a server computer, an application server, a database server, a cloud computing resource and the like. When the system 400 is implemented as the client server architecture as shown in the figure, the backend component 406 may have a web server 418 or the like that manages the connections and interactions with each computing device 402, generates HTML code to send to each computing device 402, receives data from each computing device 402, and the like. The web server 418 may be implemented in hardware or software.

The backend component 406 may include an imaging device, and/or an image analysis engine 420 that analyze pieces of medical information 410 (e.g., images). The image analysis engine 420 may analyze images, shift images, produce data 422 (e.g., data 422 such as images, e.g., shifted images and/or residual images), and the like. The image analysis engine 420 may receive/obtain the pieces of medical information 410 (e.g., images) from a computing device 402, over a computer network from a third-party, or from the storage 412 of the system 400. The data 422 may be transmitted through the network 404, e.g., for display on the one or more computing devices 402. The image analysis engine 420 may be implemented in software or hardware. When the image analysis engine 420 is implemented in software, the image analysis engine 420 (and its components) may comprise a plurality of lines of computer code that may be stored in a memory 416 and executed by a processor 414 of the backend component 406 so that the processor 414 is configured to perform the processes of the image analysis engine 420 (and its components) as described herein. When the image analysis engine 420 is implemented in hardware, the image analysis engine 420 (and its components) may comprise a microcontroller, a programmable logic device, an application specific integrated circuit, or other hardware device in which the hardware device performs the processes of the image analysis engine 420 (and its components) as described herein. The image analysis engine 420 may include an algorithm or series of algorithms that assist in generating the data 422 as discussed herein.

The one or more pieces of medical information 408 may include a medical image. The medical image may include an X-ray image, e.g., a mammogram and the like. The medical image may also or instead include magnetic resonance (MRI) images, computerized tomography (CT) scan images, ultrasound images, and so on.

The system 400 may instead be implemented as part of a standalone computer implementation. In this implementation, the image analysis engine 420 may be executed on one of the computing devices 402, e.g., by the processor 403 and memory 405, based on one or more pieces of medical information 410 stored in the computing device 402 or input into the computing device 402. The computing device 402 may have a display 426 and any other additional hardware including without limitation input/output devices such as a keyboard and a mouse. The display 426 may include a user interface, e.g., a graphical user interface. The computing device 402 may also include the processor, and a persistent storage device such as flash memory or a hard disk drive and memory, such as DRAM or SRAM, that are connected to each other. When the computing device 402 is used to implement the system and the image analysis engine 420 is implemented in software, the memory 405 may store the image analysis engine 420 and an operating system and the processor 403 of the system may execute a plurality of lines of computer code that implement the image analysis engine 420 so that the processor 403 of the computer system is configured to perform the processes of the image analysis engine 420 as described herein.

The image analysis engine 420 may, in general, receive one or more pieces of medical information 410 about a patient and, for each piece of medical information 410 for the patient, generate information related thereto (e.g., the data 422). The medical information 410 may include information regarding tissue, including without limitation any piece of human tissue or any piece of animal tissue that may have calcifications.

Example 2

Figure 5:
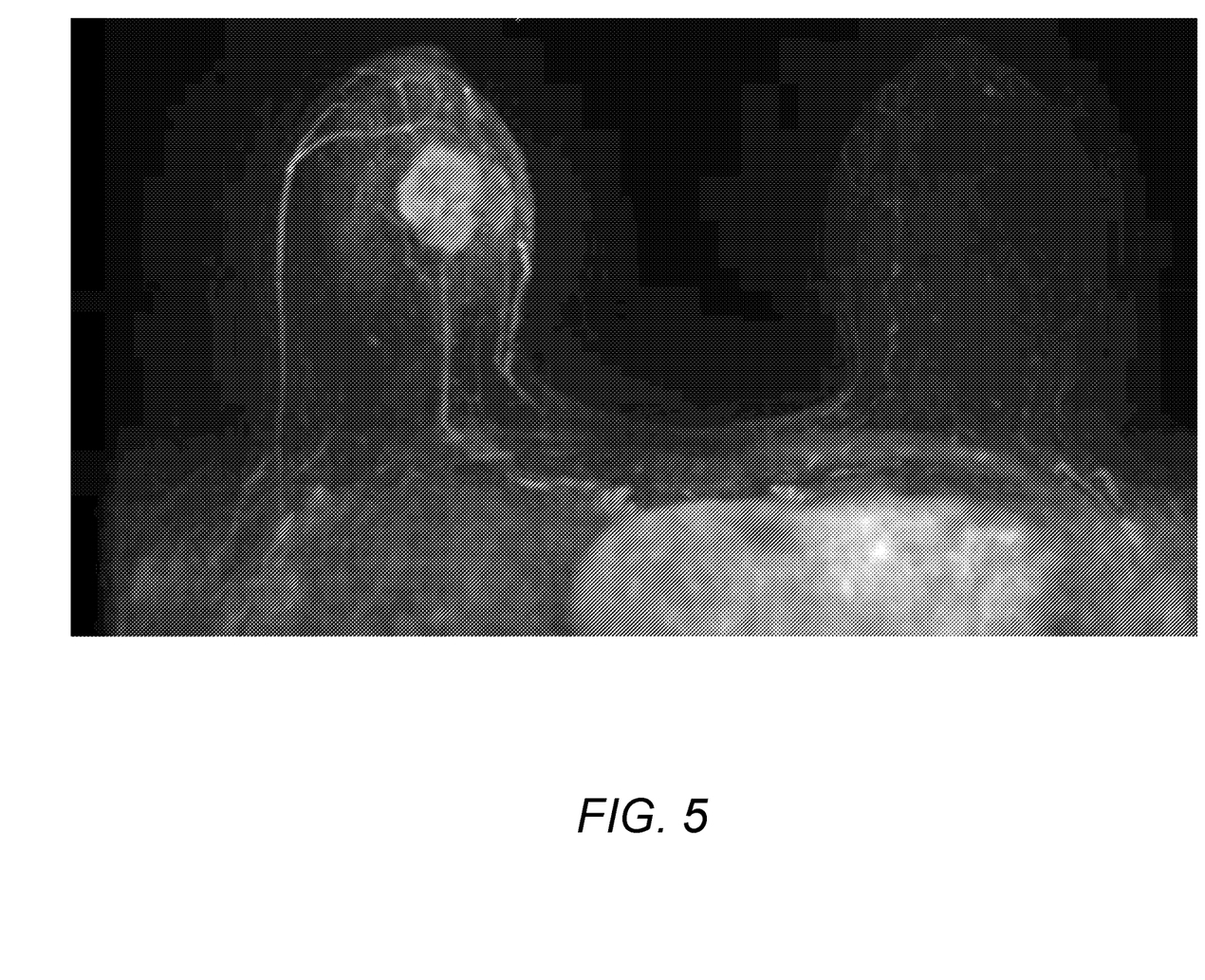
FIG. 5 shows a magnetic resonance image (MRI) of a mass in a breast.
Figure 6A:
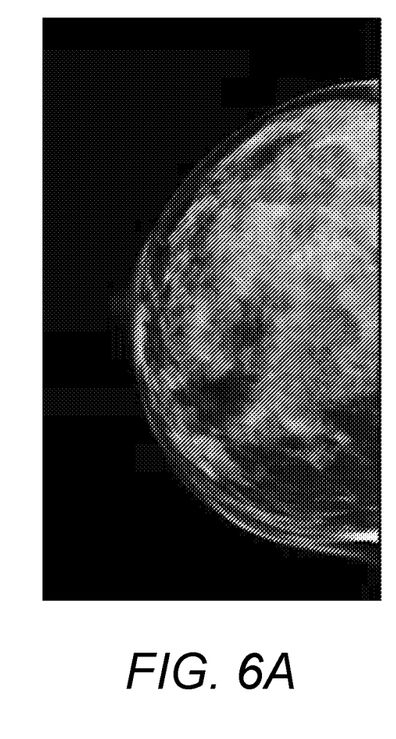
FIG. 6A shows an X-ray image of the breast depicted in FIG. 5.
Figure 6B:
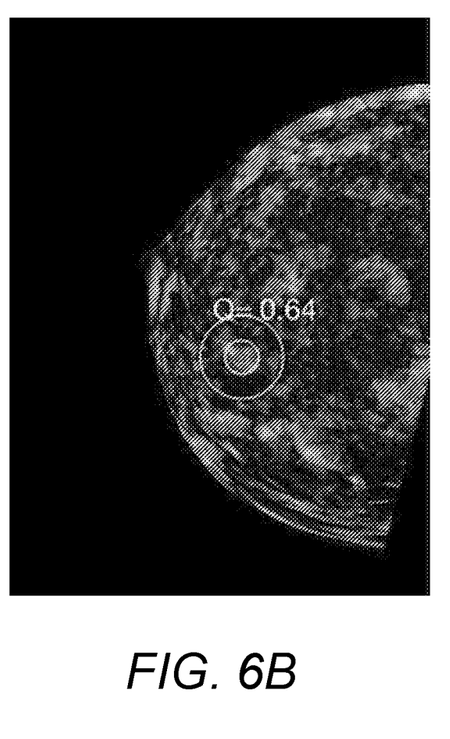
FIG. 6B shows a shifted image of the same breast, wherein a region of interest is elucidated, and a quantitative measure of that region is provided.
Figure 6C:
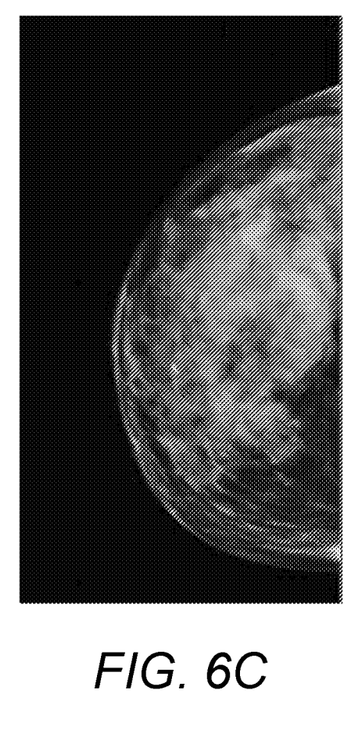
FIG. 6C shows the biopsy of the same area.

In yet another example, the methods of the present invention were applied to mammographically occult cancer case, where even after the detection of mass in MRI, the radiologists could not find evidence of mass in the mammography images. FIG. 5 shows a 4.2 cm mass by MRI of the right breast anterior depth. FIG. 6A is the screening mammography of the same patient. FIG. 6B shows the shifted version of FIG. 6A. The results of the mass algorithm (the version based on search window, e.g., that described in International Publication PCT/US2016/054074, incorporated herein by reference in its entirety) on this image indicates a region of interest with a high score. FIG. 6C is the post biopsy image for this patient, where the biopsy marker indicates the location of cancer. Comparison of FIGS. 6B and C shows that the algorithm was able to identify this mass after applying a shift, as described herein, although it is mammographically occult.

Another implementation of the methods of the present invention is to divide images into a rectangular grid and apply the shift locally to each grid. For example, one could do the shift by subtracting the neighboring grid from a given grid.

Figure 7:
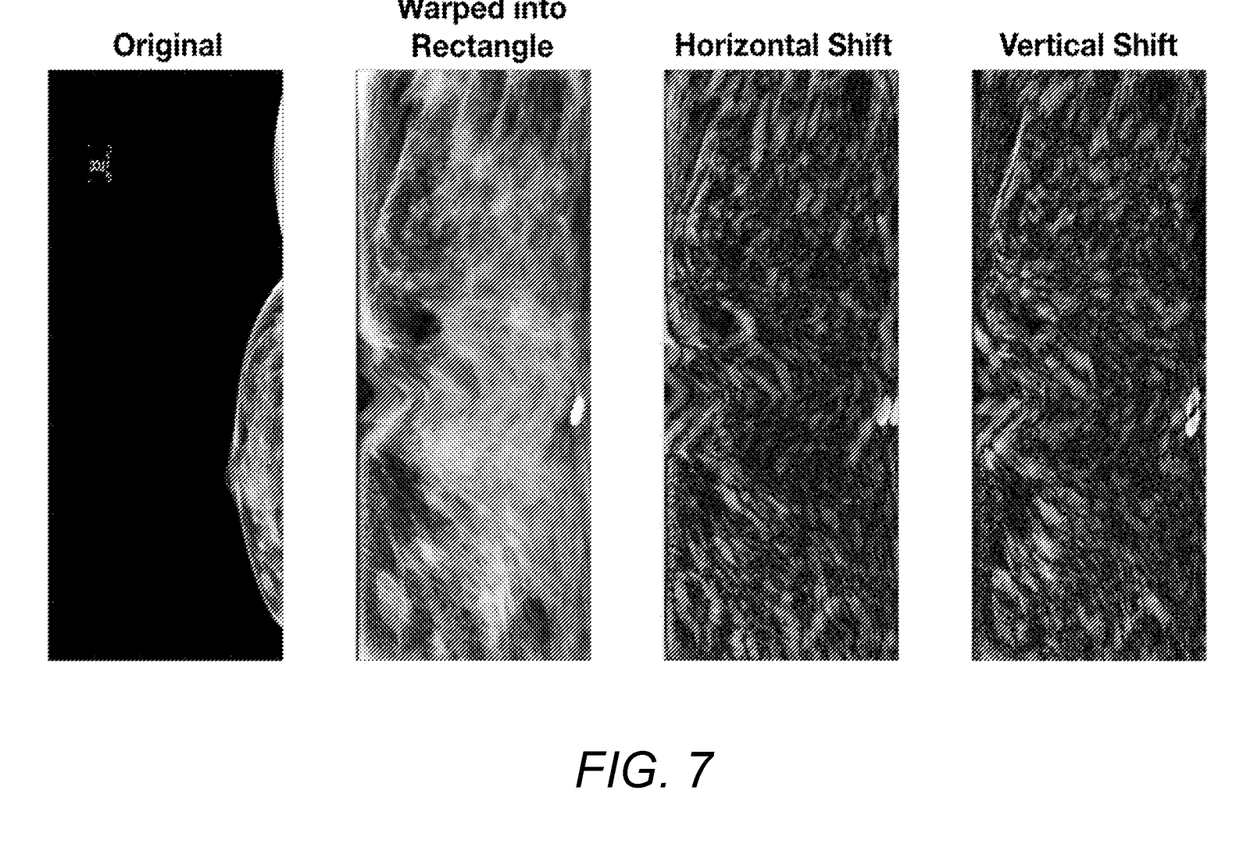
FIG. 7 shows a number of representative image shifts.

Another implementation is to apply a transformation to nonlinearly warp the image from a natural coordinate system of the object such as the breast coordinate system into a rectangle. An illustration of this technique is shown in FIG. 7. Here we select an arc of finite width based on the breast boundary (panel 1 of FIG. 7). In this example, an arc is selected between r=1.0 and r=0.3 where r=1.0 is the boundary of the breast. Then the pixels in the arc are interpolated into a rectangular image (panel 2 of FIG. 7). One can then do a horizontal shift and difference (panel 3 of FIG. 7) or a vertical shift and difference (panel 4 of FIG. 7). The horizontal shift is akin to a radial shift in the original image and the vertical shift is akin to a tangential shift in the original image. The advantage of this implementation is it reduces the need to find an optimal pivot point for the shift.

Another advantage of this implementation is that once the object has been transformed into a rectangular shape, then the convolutional nature of deep networks automatically takes into account relative translation of the objects. By warping the image onto a rectangular grid the convolution is effectively performed in the curved breast coordinate system instead of in the usual Cartesian system. The actual convolutional operation is still done in the Cartesian grid, so all the existing convolutional codes can be used unchanged, but when mapped back to the original image the filters will naturally have a curved shape. This transformation makes it simpler to represent curved filters, and more likely for a neural network to learn. For example, a small simple kernel in the Cartesian system could become something more complex like a rotational derivative approximation when mapped back to the original image.

Another application is to videos where instead of shifting the image against a variation of itself, one can apply a shift between select frames.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings.

The systems and methods disclosed herein may be implemented via one or more components, systems, servers, appliances, other subcomponents, or distributed between such elements. When implemented as a system, such systems may include an/or involve, inter alia, components such as software modules, general-purpose CPU, RAM, etc., found in general-purpose computers. In implementations where the innovations reside on a server, such a server may include or involve components such as CPU, RAM, etc., such as those found in general-purpose computers.

Additionally, the systems and methods herein may be achieved via implementations with disparate or entirely different software, hardware and/or firmware components, beyond that set forth above. With regard to such other components (e.g., software, processing components, etc.) and/or computer-readable media associated with or embodying the present implementations, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the systems and methods may be achieved via or performed by logic and/or logic instructions including program modules, executed in association with such components or circuitry, for example. In general, program modules may include routines, programs, objects, components, data structures, etc., that perform particular tasks or implement particular instructions herein. The embodiments may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, where media of any type herein does not include transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the implementations described herein or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the implementations herein, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Additionally, the words "herein," "hereunder," "above," "below," and words of similar import refer to this application as a whole and not to any particular portions of this application.

Moreover, the above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method comprising:
obtaining a first image;
analyzing the first image to detect one or more unmasked anomalies;
shifting the first image to provide a second shifted image;
comparing the first image and second shifted image;
obtaining a residual image comprising a combination of the first image and the second shifted image; and
analyzing the residual image for one or more masked anomalies, the one or more masked anomalies comprising anomalies that went undetected in the analysis of the first image for the one or more unmasked anomalies due to a presence of one or more masking features in the first image.

2. The method of claim 1, wherein the first image is a medical image.

3. The method of claim 1 or 2, wherein the image is procured by one of X-ray radiography, Magnetic Resonance Imaging, positron emission tomography, single-photon emission computed tomography, ultrasound, thermography, or photography.

4. The method of claim 3, wherein the first image includes a breast of the patient procured during a mammogram.

5. The method of claim 4, wherein the one or more masking features includes a normal breast feature.

6. The method of claim 5, wherein the normal breast feature includes one or more of a mammary gland, an artery, a vein, a lymph node, a ligament, a terminal ductal lobular unit (TDLU), and supportive tissue for the TDLU.

7. The method of claim 6, wherein the one or more masking features includes dense breast tissue.

8. The method of claim 7, wherein the first image includes a lung of the patient obtained during a lung X-ray.

9. The method of claim 8, wherein the one or more masking features includes a rib.

10. The method of claim 9, wherein shifting the first image includes rotating the first image about a point.

11. The method of claim 10, wherein the rotation is about 0.000001 degrees, about 0.00001 degrees, about 0.0001 degrees, about 0.001 degrees, about 0.01 degrees, about 0.1 degrees, about 1 degree, about 2 degrees, about 3 degrees, about 4 degrees, about 5 degrees, about 6 degrees, about 7 degrees, about 8 degrees, about 9 degrees, or about 10 degrees.

12. The method of claim 9, wherein shifting the first image includes displacement of the first image by a predetermined amount in a predetermined direction.

13. The method of claim 12, wherein the predetermined amount includes a predetermined number of pixels.

14. The method of claim 13, wherein shifting the first image includes a global shift where the same shift is applied to every point in the first image.

15. The method of claim 13, wherein shifting the first image includes a local shift where a different shift is applied to different parts of the first image.

16. The method of claim 13, wherein shifting the first image includes applying a plurality of different shifts to the first image.

17. The method of claim 16, wherein the residual image includes the shifted image overlaid on the first image.

18. The method of claim 16, wherein the residual image includes the first image overlaid on the shifted image.

19. The method of claim 18, further comprising detecting one or more masking features in the first image.

20. The method of claim 19, wherein anomalies include one or more of a calcification, a cluster of calcifications, a lesion, a mass, and a tumor.

21. The method of claim 20, wherein the one or more masking features includes one or more of tissue, a bone, cartilage, a gland, an artery, a vein, a lymph node, and a ligament.

22. A method for detecting breast cancer, the method comprising:
obtaining a first breast X-ray image;
analyzing the first image for one or more unmasked anomalies;
shifting the first image to provide a second shifted image;
obtaining a residual image comprising a combination of the first image and the second shifted image; and
analyzing the residual image for a cancer indication, the cancer indication being undetected in the analysis of the first image for cancer indication due to a presence of one or more masking features in the first image.

23. A computer program product comprising computer executable code embodied in a non-transitory computer readable medium that, when executing on one or more computing devices, performs the steps of:
obtaining a first image of a patient procured during an X-ray;
analyzing the first image for one or more unmasked anomalies;
shifting the first image to provide a shifted image;
obtaining a residual image comprising a combination of the first image and the shifted image; and
analyzing the residual image for one or more masked anomalies, the one or more masked anomalies comprising anomalies that went undetected in the analysis of the first image for the one or more unmasked anomalies due to a presence of one or more masking features in the first image.

24. A system, comprising:
an imaging device; and
a computing device in communication with the imaging device, the computing device including a processor and a memory, the memory bearing computer executable code configured to perform the steps of:
obtaining a first image of a patient from the imaging device;
analyzing the first image for one or more unmasked anomalies;
shifting the first image to provide a shifted image;
obtaining a residual image comprising a combination of the first image and the shifted image; and
analyzing the residual image for one or more masked anomalies, the one or more masked anomalies comprising anomalies that went undetected in the analysis of the first image for the one or more unmasked anomalies due to a presence of one or more masking features in the first image.

* * * * *